(12) United States Patent
Sheldon

(10) Patent No.: US 8,170,666 B2
(45) Date of Patent: May 1, 2012

(54) METHOD FOR SCHEDULING ATRIAL-VENTRICULAR CONDUCTION CHECKS IN MINIMUM VENTRICULAR PACING

(75) Inventor: Todd J. Sheldon, North Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 379 days.

(21) Appl. No.: 12/540,632

(22) Filed: Aug. 13, 2009

(65) Prior Publication Data

US 2011/0040346 A1    Feb. 17, 2011

(51) Int. Cl.
*A61N 1/362* (2006.01)
(52) U.S. Cl. ............................................. 607/9; 607/27
(58) Field of Classification Search .................. 607/9, 27
See application file for complete search history.

(56) References Cited

U.S. PATENT DOCUMENTS

| | | | |
|---|---|---|---|
| 5,117,824 A | 6/1992 | Keimel et al. | |
| 5,318,594 A * | 6/1994 | Limousin et al. | ............ 607/9 |
| 5,417,714 A | 5/1995 | Levine et al. | |
| 6,772,005 B2 | 8/2004 | Casavant et al. | |
| 7,218,965 B2 | 5/2007 | Casavant et al. | |
| 7,248,924 B2 | 7/2007 | Casavant et al. | |
| 7,565,196 B2 | 7/2009 | Sheldon et al. | |
| 2002/0082646 A1 | 6/2002 | Casavant et al. | |
| 2004/0143299 A1 | 7/2004 | Casavant et al. | |
| 2005/0240235 A1 | 10/2005 | Limousin et al. | |
| 2007/0191891 A1 | 8/2007 | Burnes et al. | |

OTHER PUBLICATIONS (PCT/US2010/042674) PCT Notification of Transmittal of the International Search Report and the Written Opinion of the International Searching Authority, 2011.

* cited by examiner

*Primary Examiner* — George Evanisko
(74) *Attorney, Agent, or Firm* — Michael C. Soldner

(57) ABSTRACT

A medical device and associated method deliver cardiac pacing in a dual chamber pacing mode and schedule an atrial-ventricular (AV) conduction check during the dual chamber pacing mode to detect the presence of AV conduction. If AV conduction is detected during the scheduled AV conduction check, the medical device switches to an atrial pacing mode and switches back to the dual chamber pacing mode in response to an absence of AV conduction during the atrial pacing mode. The detected AV conduction is identified as a false positive detection in response to the pacing mode switch to the dual chamber pacing mode occurring within a predetermined interval of time from detecting the AV conduction.

18 Claims, 7 Drawing Sheets

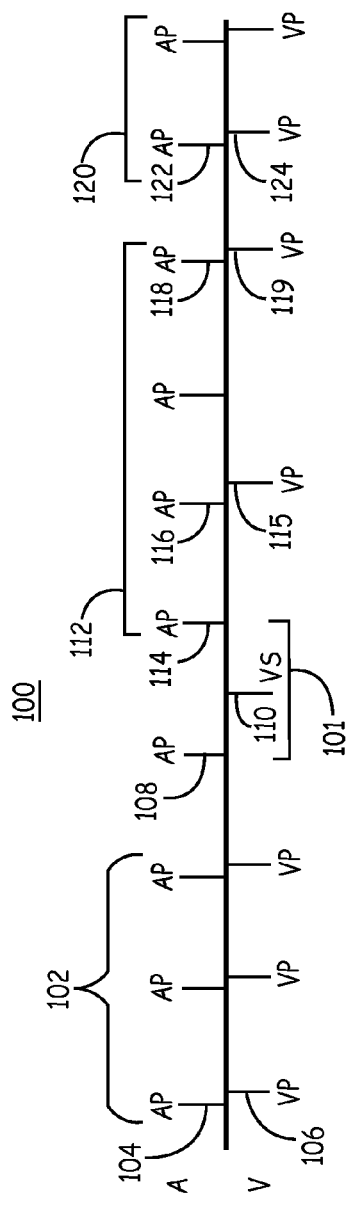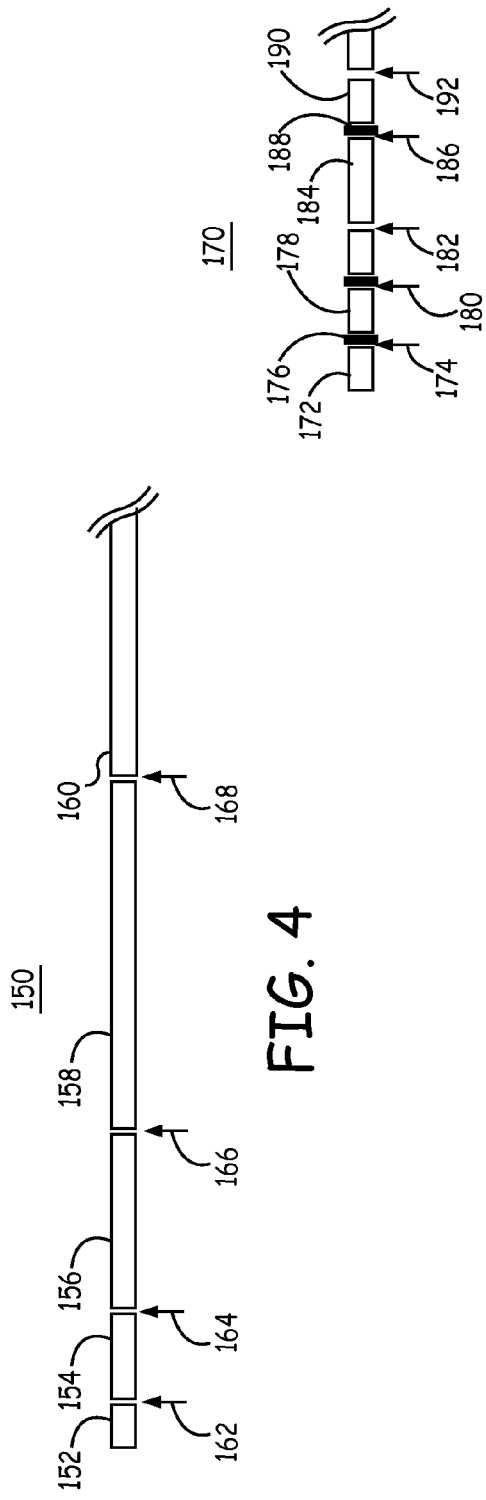

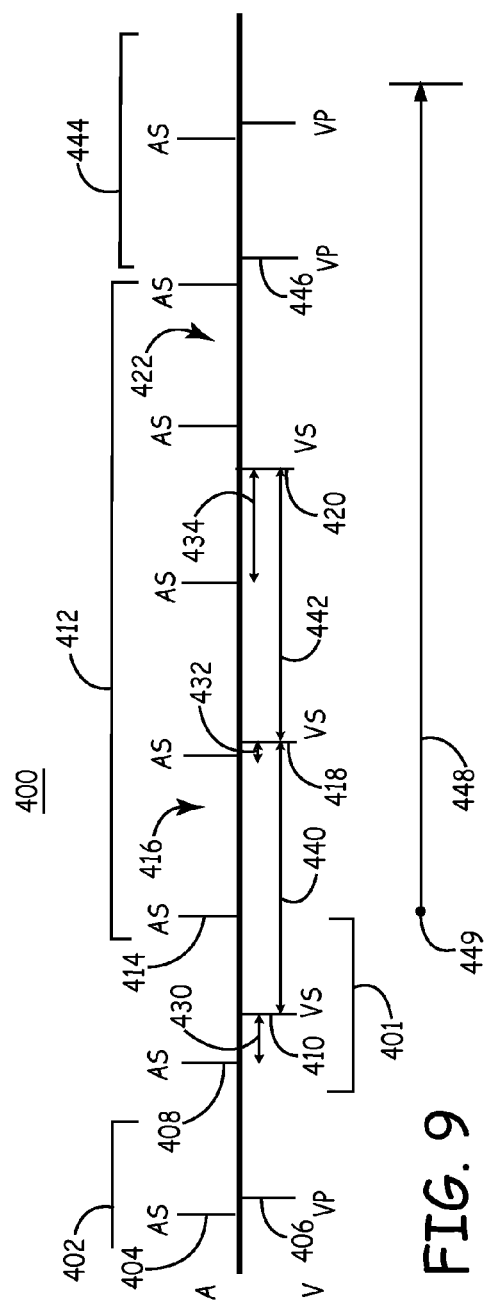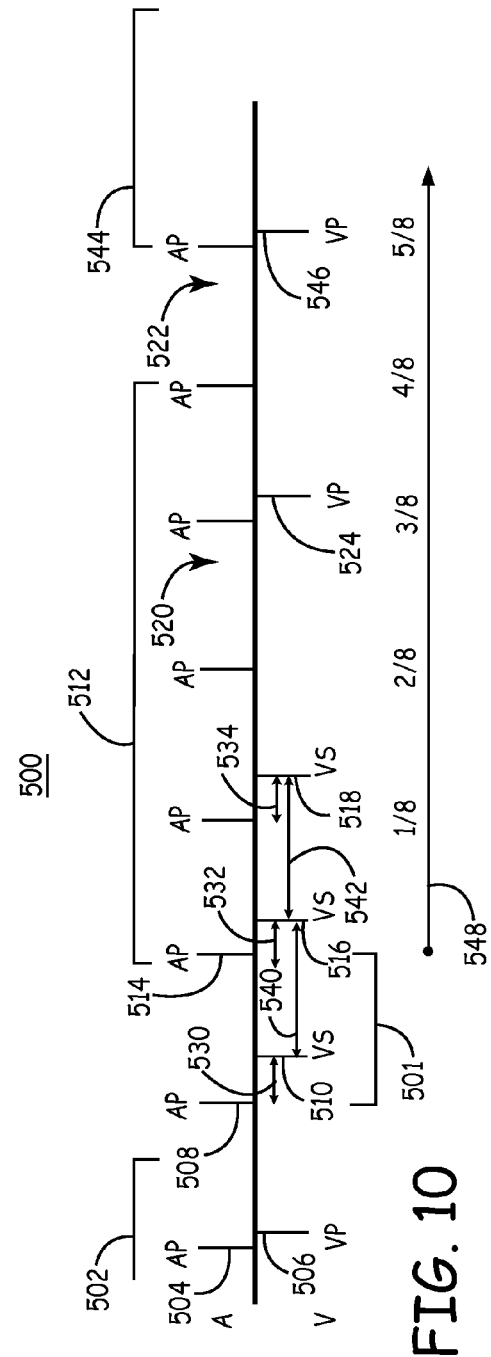

METHOD FOR SCHEDULING ATRIAL-VENTRICULAR CONDUCTION CHECKS IN MINIMUM VENTRICULAR PACING

TECHNICAL FIELD

The disclosure relates generally to implantable medical devices and, in particular, to automatic scheduling of atrial-ventricular conduction checks in implantable medical devices.

BACKGROUND

Naturally-conducted or intrinsic ventricular depolarizations have been recognized as being preferable over ventricular pacing in general and pacing in the right ventricular apex in particular. In order to minimize or greatly reduce ventricular pacing, pacing protocols have been developed that, in general, utilize an atrial based timing mode that promotes intrinsic conduction to the ventricles whenever possible. Illustrative protocols are described in U.S. Pat. No. 7,218,965 (Casavant), U.S. Pat. No. 6,772,005 (Casavant), and U.S. Pat. No. 7,248,924 (Casavant), all of which are incorporated herein by reference in their entireties.

Atrial based pacing performed in the context of minimizing ventricular pacing as discussed above reverts to dual chamber pacing in the event of AV conduction block. After switching to a dual chamber pacing mode, such as DDD, periodic AV conduction checks are scheduled. When AV conduction is again detected as signified by a ventricular sensed event following an atrial pacing pulse, atrial pacing is resumed to allow the more desirable naturally-conducted ventricular activation to occur.

An AV conduction check can sometimes result in a false positive detection of AV conduction in patients having AV conduction block and an idioventricular rhythm, premature ventricular contractions (PVCs), or other ventricular beats arising from the ventricular region of the heart and not conducted from the atrium. An idioventricular depolarization or a PVC may coincidentally occur during an AV conduction check, signifying, incorrectly, that AV conduction is intact.

In this situation, a false positive detection of AV conduction will cause conversion from dual chamber to atrial pacing and resets an AV conduction check timer. Since AV block is actually present, the pacemaker will quickly return to a dual chamber pacing mode, and a newly scheduled AV conduction check will again be performed. Frequent pacing mode switching and AV conduction checks are unnecessarily performed. Accordingly, a need remains for a device and method for delivering minimum ventricular pacing (MVP) that reduces the likelihood of frequent and unnecessary pacing mode switching and AV conduction checks.

BRIEF DESCRIPTION OF THE DRAWINGS

FIG. 3 is a timeline depicting atrial and ventricular sense and pace events during an episode of minimum ventricular pacing.

FIG. 4 is a timeline depicting the occurrence of scheduled AV conduction checks during dual chamber pacing when minimum ventricular pacing is enabled.

FIG. 5 is a timeline illustrating scheduled AV conduction checks that occur when AV conduction is falsely detected.

FIG. 9 is a timeline illustrating the situation of an idioventricular rhythm causing a false positive AV conduction detection.

FIG. 10 is a time line illustrating the situation of highly intermittent AV conduction resulting in a positive AV conduction check.

DETAILED DESCRIPTION

Figure 1:
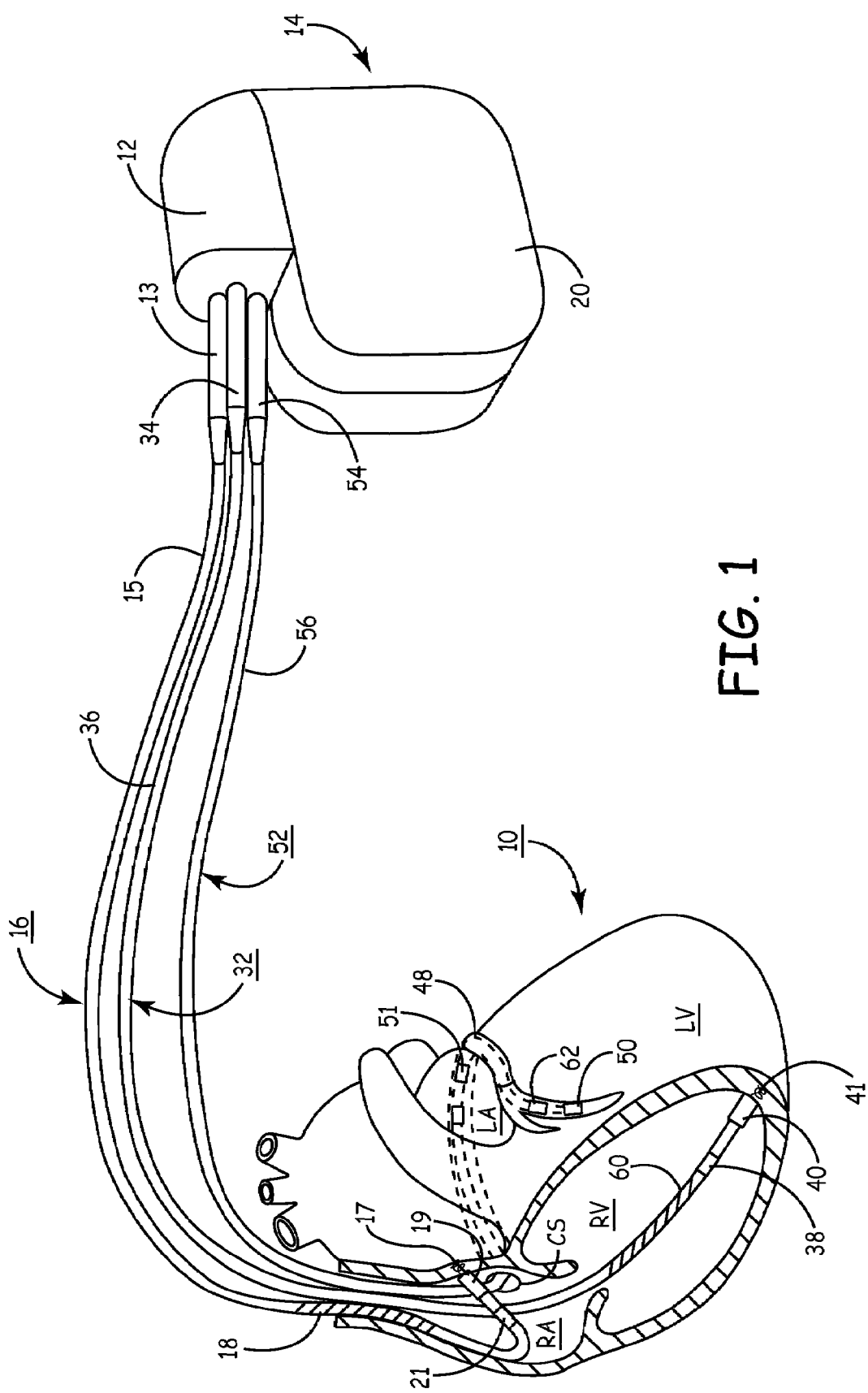
FIG. 1 depicts an implantable, cardiac stimulation device in which monitoring and pacing methods described herein may be implemented.

In the following description, references are made to illustrative embodiments. It is understood that other embodiments may be utilized without departing from the scope of the disclosure. For purposes of clarity, the same reference numbers are used in the drawings to identify similar elements. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

As used herein, an atrial based pacing mode is a mode that is programmed to sense and pace in the atria and only sense in the ventricles. True single chamber atrial pacing would imply that only a single lead is present and ventricular activity may not be sensed in the ventricle nor would ventricular pacing be deliverable. In the present context an IMD operating in an atrial based mode includes at least ventricular sensing capabilities. Such a device would generally include ventricular pacing as well. However, in order to deliver ventricular pacing the device would switch pacing modes from the atrial only pacing mode to a dual chamber pacing mode, such as DDD.

FIG. 1 depicts an implantable medical device (IMD) 14 in which monitoring and pacing methods described herein may be implemented. Various embodiments of the disclosure may be implemented in numerous types of implantable medical devices capable of sensing cardiac signals and delivering pacing pulses including pacemakers and implantable cardioverter defibrillators (ICDs). IMD 14 is provided for sensing intrinsic heart activity and delivering cardiac stimulation pulses in the form of pacing and may deliver cardioversion or defibrillation therapy, as appropriate, to one or more heart chambers.

IMD 14 is shown in communication with a patient's heart 10 by way of three leads 16, 32 and 52. The heart 10 is shown in a partially cut-away view illustrating the upper heart chambers, the right atrium (RA) and left atrium (LA), the lower heart chambers, the right ventricle (RV) and left ventricle (LV), and the coronary sinus (CS) in the right atrium leading into the great cardiac vein 48, which branches to form inferior cardiac veins. Leads 16, 32 and 52 are connected to internal circuitry of IMD 14 via connectors 17, 34 and 54, respectively, inserted into IMD connector block 12, thereby coupling IMD 14 with the RA, the RV and the LV. Each lead has at least one electrical conductor and pace/sense electrode. A remote indifferent can electrode can be formed as part of the outer surface of the IMD housing 20. The pace/sense electrodes and the remote indifferent can electrode can be selectively employed to provide a number of unipolar and bipolar pace/sense electrode combinations for pacing and sensing functions.

RA lead 16 is passed into the RA chamber and is shown provided with a RA tip electrode 19 and RA ring electrode 21 which are coupled to IMD circuitry housed within housing 20 via insulated conductors extending within lead body 15. RA tip electrode 19 and RA ring electrode 21 may be used in a bipolar fashion, or in a unipolar fashion with IMD housing 20, for achieving RA stimulation and sensing of RA EGM signals. RA lead 16 is optionally provided with a coil electrode 18 that may be used for delivering high voltage cardioversion/defibrillation pulses to heart 10 in response to the detection of tachycardia or fibrillation.

RV lead 32 is passed into the RV and carries RV tip electrode 40 and RV ring electrode 38 for stimulation in the RV and sensing of RV EGM signals. RV lead 32 may be fixed in place in the RV apex by a distal fixation member 41. RV lead 32 optionally carries a high-voltage coil electrode 60 for use in cardioverting and defibrillating heart 10.

Coronary sinus lead 52 is passed into a cardiac vein 48 to extend the distal LV tip electrode 50 and ring electrode 62 alongside the LV chamber to achieve LV stimulation and sensing of LV EGM signals. In some embodiments, LV CS lead 52 could bear a proximal LA pace/sense electrode 51 positioned along CS lead body 56 such that it is disposed proximate the LA for use in stimulating the LA and/or sensing LA EGM signals.

In addition to the lead-mounted electrodes, IMD 14 may include one or more subcutaneous cardiac sensing electrodes (not shown) formed as uninsulated portions of the IMD housing 20 or included in the connector block 12. While a particular IMD system with associated leads and electrodes is illustrated in FIG. 1, numerous implantable cardiac pacemaker or ICD system configurations are possible, which may include one or more leads deployed in transvenous, subcutaneous, or epicardial locations for sensing and pacing in the atrial and ventricular regions of the heart. The lead and electrode arrangements will depend on the particular application. Methods described herein may also be implemented in a subcutaneous IMD in which electrodes are formed as a part of the device housing and/or carried by subcutaneous leads.

IMD 14 is shown as a multi-chamber device capable of sensing and stimulation in three or all four heart chambers. It is understood that IMD 14 may be modified to operate as a dual chamber device capable of operating in both single-chamber and dual chamber pacing modes. In the illustrative embodiments, described herein, methods for delivering minimum ventricular pacing generally relate to a pacemaker or ICD at least capable of dual chamber sensing and pacing.

Figure 2:
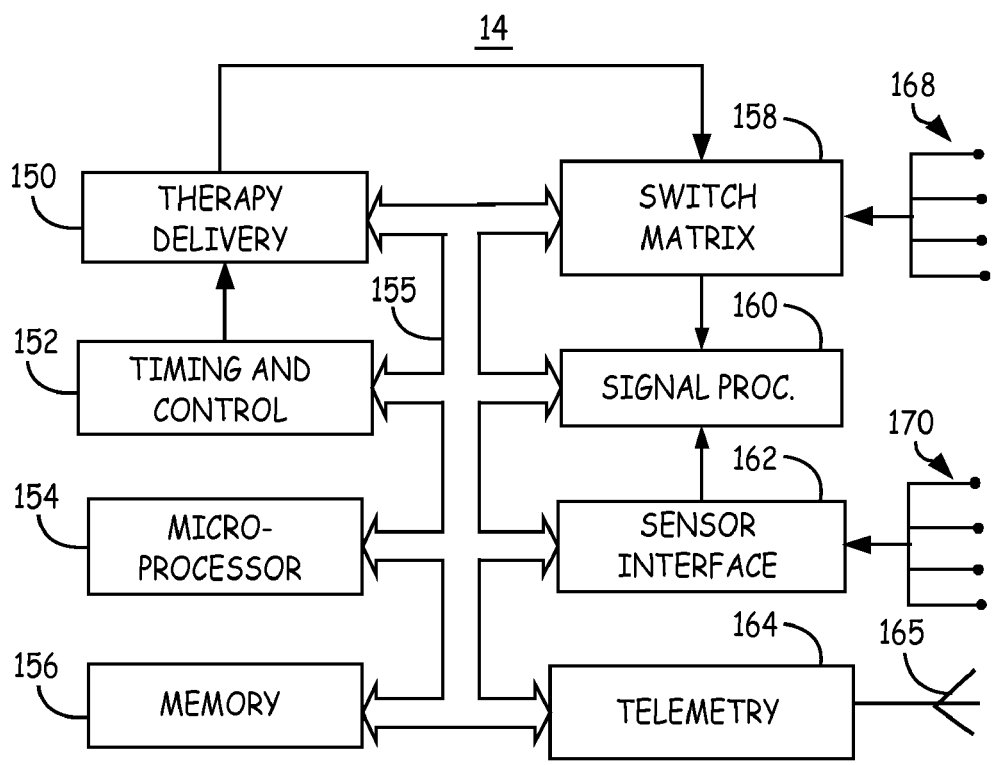
FIG. 2 is a functional block diagram of the implantable device shown in FIG. 1 according to one embodiment.

FIG. 2 is a functional block diagram of the IMD 14 shown in FIG. 1 according to one embodiment. IMD 14 generally includes timing and control circuitry 152 and an operating system that may employ microprocessor 154 or a digital state machine for timing sensing and therapy delivery functions in accordance with a programmed operating mode. Microprocessor 154 and associated memory 156 are coupled to the various components of IMD 14 via a data/address bus 155. IMD 14 includes therapy delivery module 150 for delivering electrical stimulation therapies, such as cardiac pacing therapies and arrhythmia therapies including cardioversion/defibrillation shocks and anti-tachycardia pacing (ATP), under the control of timing and control 152.

Therapy delivery module 150 is typically coupled to two or more electrodes 168 via an optional switch matrix 158. Electrodes 168 may correspond to any of the electrodes shown in FIG. 1. Switch matrix 158 may be used for selecting which electrodes and corresponding polarities are used for delivering electrical stimulation pulses.

Cardiac electrical signals are sensed for use in determining when an electrical stimulation therapy is needed and in controlling a stimulation mode and the timing of stimulation pulses. Electrodes 168 used for sensing are coupled to signal processing circuitry 160. Signal processor 160 includes sense amplifiers and may include other signal conditioning circuitry and an analog-to-digital converter. Electrical signals may then be used by microprocessor 154 or other control circuitry for detecting physiological events, such as detecting and discriminating cardiac arrhythmias or detecting the need for pacing. Signal processing circuitry 160 may include event detection circuitry generally corresponding to R-wave detection circuitry as disclosed in U.S. Pat. No. 5,117,824 (Keimel, et al.), hereby incorporated herein by reference in its entirety.

IMD 14 is additionally coupled to one or more physiological sensors 170. Signals from sensors 170 are received by a sensor interface 162 which provides sensor signals to signal processing circuitry 160. Sensor signals are used by microprocessor 154 for detecting physiological events or conditions. For example, IMD 14 may monitor patient activity using an activity sensor included in physiological sensors 170. Monitored signals may be used for sensing the need for delivering or adjusting cardiac pacing under control of microprocessor 154. Monitored sensor signals may be analyzed to obtain patient or device-related diagnostic data stored by IMD 14 and made available to a clinician.

In various embodiments, IMD 14 includes rate responsive pacing in which an activity sensor, oxygen sensor, respiration sensor, or other sensor generating a signal correlated to changes in metabolic demand, referred to herein generally as a "demand sensor", or any combination of demand sensors, is used to compute a sensor-indicated rate (SIR). Timing and control module 152 responds to the SIR by adjusting a pacing rate up or down between a programmed lower rate and a maximum upper rate. The methods described herein for controlling minimum ventricular pacing may be implemented in combination with rate-responsive pacing that utilizes a demand sensor-indicated rate.

The IMD operating system includes associated memory 156 for storing a variety parameter values that are used by microprocessor 154 for controlling device functions. Algorithms and control parameters used for determining a SIR and delivering rate responsive pacing, detecting arrhythmias, delivering arrhythmia therapy, and controlling minimum ventricular pacing may be stored in memory 156. The memory 156 may also be used for storing data compiled from sensed EGM and physiological signals and/or relating to device operating history for telemetry out on receipt of a retrieval or interrogation instruction.

IMD 14 further includes telemetry circuitry 164 and antenna 165. Programming commands or data are transmitted during uplink or downlink telemetry between IMD telemetry circuitry 164 and external telemetry circuitry included in a programmer or monitoring unit.

FIG. 3 is a timeline 100 depicting atrial and ventricular sense and pace events during an episode of minimum ventricular pacing. Atrial (A) events are depicted along the upper portion of timeline 100 and ventricular (V) events are depicted along the lower portion of timeline 100. Initially, dual chamber pacing 102 is delivered including atrial pace events 104 and ventricular pace events 106 delivered at a programmed pacing rate (AA or VV interval), with atrial and ventricular pace events 102 and 104 separated by an atrial-ventricular interval.

At a scheduled time, an atrial-ventricular (AV) conduction check 101 is performed. An atrial ventricular conduction check is performed at scheduled intervals during dual chamber pacing to determine if AV conduction is intact. If AV conduction is detected, the pacing mode is switched from dual chamber pacing to single chamber atrial pacing to give preference to naturally-conducted ventricular depolarizations over ventricular pacing. The AV conduction check may be performed by delivering a single atrial pacing pulse 108 in an atrial-only pacing mode, such as AAI, for one cardiac cycle. If an intrinsic ventricular sense event 110 occurs any time prior to the next atrial event 114 (which may be a sensed or scheduled paced atrial event), AV conduction is detected. If no ventricular sense event occurs before the next atrial event 114, AV block is detected and dual chamber pacing would continue.

In alternative embodiments, an AV conduction check 101 may be performed by extending the AV interval following an atrial pacing pulse 108. The AV interval may be extended to a maximum available interval to allow an intrinsically-conducted ventricular depolarization to occur prior to the ventricular escape interval time out. If a ventricular sensed event occurs before the scheduled ventricular pacing pulse, AV conduction is detected.

In response to detecting AV conduction, the pacing mode switches to an atrial-only pacing mode 112. In the example shown, however, the ventricular sense event 110 is associated with an idioventricular rhythm, a premature ventricular contraction, or other intrinsic depolarization originating in the ventricles that is not conducted from the atria. The coincidental sensing of the ventricular event 110 during the AV conduction check results in a false positive detection of AV conduction. As a result, during the atrial only pacing mode 112, ventricular sense events do not occur as expected if AV conduction were intact.

Following an atrial pacing pulse 114, no ventricular event is sensed. During the atrial-only pacing mode 112, a ventricular pacing pulse may not be delivered for one or more atrial pacing cycles. However, to avoid ventricular asystole for more than one cardiac cycle, a ventricular pacing pulse 115 may be delivered following the next atrial pacing pulse 116. A second atrial-only pacing cycle occurs ending on atrial pacing pulse 118 in which no ventricular event is sensed. As a result, another ventricular pacing pulse 119 is delivered on the next cardiac cycle to prevent more than one cycle of ventricular asystole.

In response to no ventricular sensed event occurring during at least two cycles of the atrial-only pacing mode 112, the IMD controller switches the pacing mode back to dual chamber pacing 120 such that both atrial pacing pulses 122 and ventricular pacing pulses 124 are delivered again. The pacing mode switches back to dual chamber pacing 120 relatively quickly, for example within approximately fifteen seconds or less, when a false positive AV conduction detection is made.

In various embodiments, the criteria for causing a pacing mode switch back to dual chamber pacing may vary. In one embodiment, at least two out of four consecutive cycles during atrial-only pacing in which AV conduction is absent will trigger a mode switch back to dual chamber pacing. Thus, in FIG. 3, after the second atrial pacing cycle ending with atrial pacing pulse 118 occurs with no ventricular sense event, the atrial-only pacing mode 112 switches to dual chamber pacing 120. In other embodiments, one or more atrial-only pacing cycle with no ventricular sense event may be required to convert back to dual chamber pacing. As such, in various embodiments, the duration of atrial only pacing 112 provided in response to a false positive AV conduction check will vary depending on the criteria set for converting back to a dual chamber pacing mode. Additional PVCs or idioventricular depolarizations sensed during the atrial only pacing mode may also delay conversion back to the dual chamber mode by one or more cardiac cycles. Generally speaking however, the conversion back to the dual chamber mode will occur quickly, in less than one minute or even shorter intervals.

FIG. 4 is a timeline 150 depicting the occurrence of scheduled AV conduction checks during dual chamber pacing when minimum ventricular pacing is enabled. During an AV conduction check performed as a single AAI pacing cycle in the presence of AV block, ventricular asystole will occur for that pacing cycle cycle. As such, it is generally desirable to avoid highly frequent AV conduction checks to avoid frequent cycles of ventricular asystole. The frequent cycles of ventricular asystole associated with frequent AV conduction checks can be concerning or misunderstood when observed during ECG monitoring by a nurse or other caregiver. Frequent AV conduction checks may be perceivable by the patient as a slowing of the heart rate and may cause mild symptoms. In current practice, AV conduction checks are typically scheduled at increasing time intervals when AV block is detected to avoid repetitive conduction checks at relatively short intervals.

As shown in FIG. 4, AV conduction checks 162, 164, 166 and 168 are repeated at successively increasing time intervals 152, 154, 156, and 158 during dual chamber pacing. For example, following a mode switch to dual chamber pacing, the first AV conduction check 162 may be performed after an initial short interval 152 of dual chamber pacing. For example interval 152 may be approximately one minute. If AV conduction is not detected, the next AV conduction check 164 occurs after an increased interval 154 of dual chamber pacing, for example approximately two minutes. As long as AV conduction is not detected, each successive interval of dual chamber pacing 156, 158, 160 is increased in length before the next scheduled AV conduction check 166, 168 and so on. In one embodiment, each interval 156, 158, 160 and so on is doubled in length.

The time intervals between AV conduction checks may be successively increased up to some maximum interval, such as an interval between approximately 12 and 24 hours, e.g., 16 hours. If AV conduction is detected during any of the AV conduction checks, the pacing mode is switched to an atrial-only pacing mode. If ventricular events are not sensed during atrial pacing for a predetermined number of atrial pacing cycles, a mode switch back to dual chamber pacing results in the scheduled AV conduction checks beginning again at the shortest initial interval 152, e.g. one minute and successively increasing again as shown in FIG. 4 until AV conduction is detected.

FIG. 5 is a timeline 170 illustrating scheduled AV conduction checks that might occur when AV conduction is falsely detected. An initial interval 172 of dual chamber pacing occurs after a mode switch from an atrial only pacing mode to a dual chamber pacing mode in response to ventricular events not being sensed during a predetermined number of cycles of the atrial only pacing mode. An AV conduction check 174 is performed after the initial interval 172 of dual chamber pacing. AV conduction is falsely detected due to an idioventricular rhythm, premature ventricular contraction, or other non-conducted ventricular depolarization coincident with the AV conduction check 174. The false positive AV conduction detection causes a mode switch to atrial only pacing 176. The atrial only pacing 176 is brief because AV block is actually present, resulting in another mode switch to occur within a short period of time, e.g. ten to fifteen seconds, back to dual chamber pacing 178. The mode switch back to a dual chamber pacing mode 178 causes the scheduled AV conduction checks to begin again after an initial short interval 178 (e.g. one minute) of dual chamber pacing.

In the illustrative example shown, the next conduction check 182 does not result in a detection of AV conduction. The next AV conduction check is therefore scheduled to occur after a longer interval 184 (e.g. approximately two minutes) of dual chamber pacing. However, at AV conduction check 186, AV conduction is again falsely detected resulting in a brief interval 188 of atrial-only pacing and another mode switch back to dual chamber pacing during interval 190. AV conduction checks are again scheduled at successively increasing intervals, beginning with the first AV conduction check 192 after the initial short interval 190 of dual chamber pacing.

FIG. 5 illustrates the situation of frequent mode switching that may occur in a patient having frequent PVCs or an idioventricular rate that results in depolarizations of ventricular origin (in contrast to being conducted from the atria) occurring frequently enough that they are coincidentally sensed during AV conduction checks. The resulting in false positive AV conduction detection causes frequent mode switches and resets the scheduled AV conduction check intervals to an initial short interval. Such frequent mode switching and AV conduction checks may also be triggered in patients that have highly intermittent AV conduction, such as patients having second degree AV block.

This frequent mode switching and restarting of the scheduled AV conduction checks at an initial short interval may be sustained for minutes, hours or even days. While FIG. 5 may represent a somewhat extreme case, it is possible that in some patients, mode switching and AV conduction checks may occur several or many times per hour. Such frequent mode switching and AV conduction checks generally results in inconsistencies in the heart rhythm that can be confusing when observed on an ECG and may be perceivable by a patient and mildly symptomatic.

Figure 6:
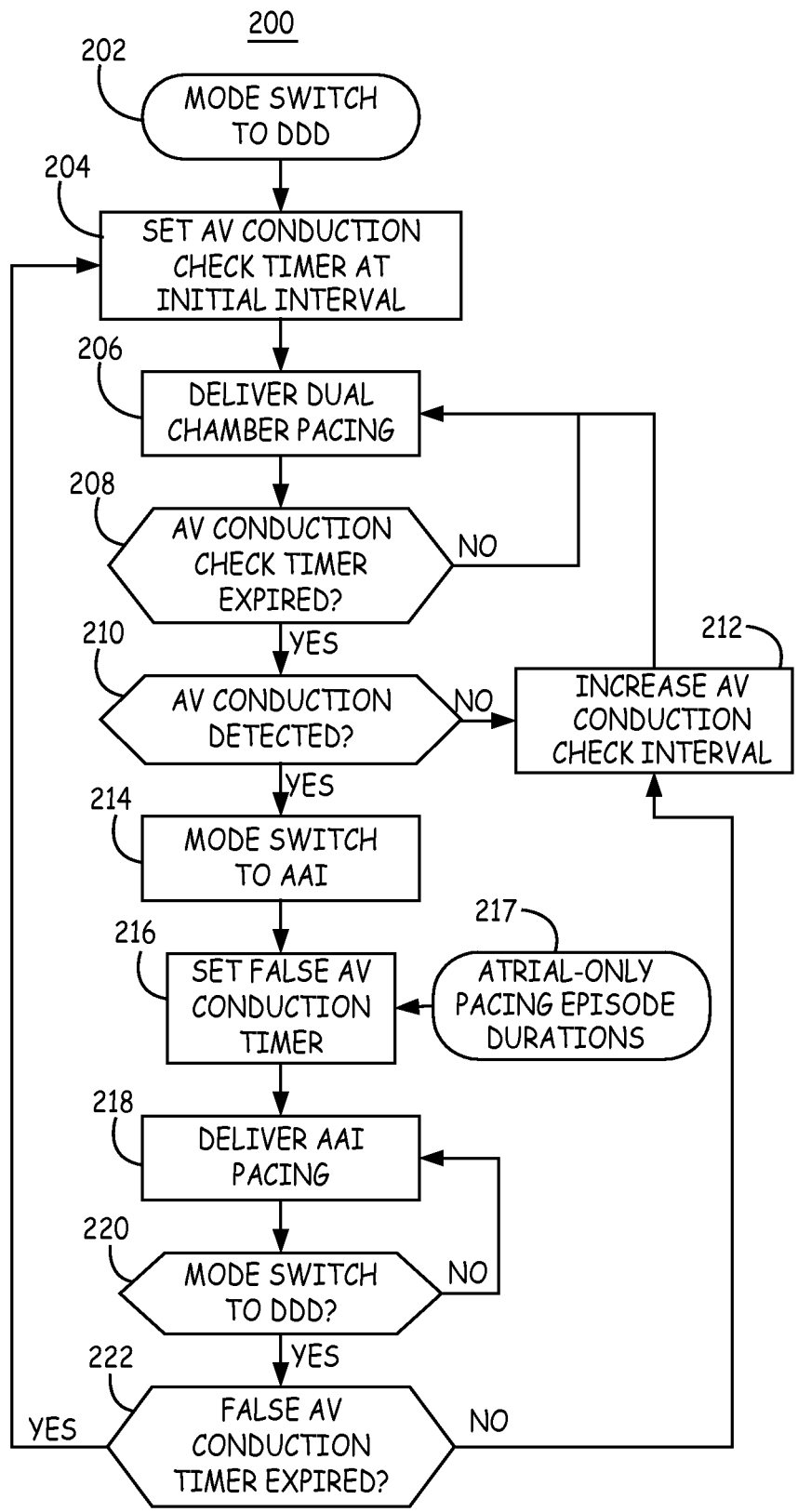
FIG. 6 is a flow chart of a method for controlling minimum ventricular pacing according to one embodiment.

FIG. 6 is a flow chart 200 of a method for controlling minimum ventricular pacing according to one embodiment. Flow chart 200 is intended to illustrate the functional operation of the device, and should not be construed as reflective of a specific form of software or hardware necessary to practice the methods described herein. It is believed that the particular form of software will be determined primarily by the particular system architecture employed in the device and by the particular detection and therapy delivery methodologies employed by the device. Providing software to accomplish the described functionality in the context of any modern medical device, given the disclosure herein, is within the abilities of one of skill in the art.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

The method shown in FIG. 6 minimizes the likelihood of frequent mode switching and frequent AV conduction checks that can otherwise occur in the presence of an idioventricular rhythm, PVCs or other non-conducted ventricular depolarizations causing false positive AV conduction detections. Method 200 is executed when minimum ventricular pacing is enabled. Method 200 and other methods described herein are not limited to operate in the context of minimum ventricular pacing, however, and may be implemented in any pacing therapy that includes performing AV conduction checks. At block 202, a dual chamber pacing mode is initiated, for example when an initial mode switch from an atrial-only pacing mode occurs due to the absence of ventricular sense events.

At block 204, an AV conduction check is scheduled in response to the mode switch to dual chamber pacing. The conduction check may be scheduled by setting a timer to an initial, shortest interval of a schedule of successively increasing conduction check intervals. For example, the first conduction check may be scheduled to occur approximately one minute after initiating dual chamber pacing.

Dual chamber pacing is delivered at block 206 until the AV conduction check timer expires as determined at block 208. The AV conduction check is performed at block 210 as generally described above. Briefly, a single atrial-only pacing cycle may be delivered. If no ventricular event is sensed prior to the next atrial event, AV conduction is not detected. In other words, a negative AV conduction detection is made. In response to the negative result, the AV conduction check interval is increased, at block 212, to the next, longer interval of a schedule of progressively increasing conduction check intervals. For example, the AV conduction check timer may be set to an interval increased from the initial shortest interval of approximately one minute to approximately two minutes. Dual chamber pacing continues at block 206, with the next conduction check performed after the conduction check timer expires.

This process (blocks 204 through 212) continues until AV conduction is positively detected at block 210 during an AV conduction check. At block 214, the IMD controller switches the pacing mode to an atrial-only pacing mode, such as AAI, in response to the positive AV conduction detection.

At block 216, a false AV conduction timer is set. The false AV conduction timer is set to a relatively short interval, for example approximately one minute or less. In one embodiment the false AV conduction timer is set to approximately 15 seconds, though other intervals could be used including approximately 10 seconds, approximately 20 seconds, approximately 30 seconds, and so on. The interval selected may depend at least in part on the criteria set for converting back to a dual chamber pacing mode. For example, if only two atrial-only pacing intervals without a ventricular sense event are required for triggering a mode-switch back to dual chamber pacing, the false AV conduction timer may be set to a relatively shorter interval, for example 15 seconds, than when a larger number of cycles, e.g. four cycles, without a ventricular sense event are required to trigger the mode switch. Alternatively, the false AV conduction timer may be defined as a number of pacing cycles during the atrial-only pacing mode rather than an interval in units of time.

The IMD delivers atrial-only pacing at block 218 and continues in the atrial-only pacing mode until AV block is detected (no ventricular sense event occurring between a predetermined number of atrial pace/sense events). When AV block is detected as evidenced by an absence of ventricular sensed events, a mode switch back to dual chamber pacing occurs. If a mode switch occurs at block 220, and the false AV conduction timer has expired as determined at block 222, the AV conduction previously detected at block 210 is deemed valid. Method 200 continues by returning to block 204 to schedule the next AV conduction check at the initial, shortest time interval of the schedule of progressively increasing conduction check intervals. Dual chamber pacing is delivered at block 206.

If, however, the false AV conduction timer has not expired (block 222) when the mode switch back to dual chamber pacing occurs (block 220), the next AV conduction check is scheduled at block 212 at an interval of time that is increased relative to the default, initial shortest conduction test interval that would normally be set at block 204. The AV conduction positively detected at block 210 and subsequently followed by an early conversion back to dual chamber pacing was likely a false detection caused by the presence of a non-conducted ventricular depolarization occurring coincidentally during the AV conduction check. The early return to dual chamber pacing would normally reset the AV conduction check schedule to an initial, shortest time interval (block 204). Method 200, however, avoids or minimizes frequent AV conduction checks and mode switching caused by false positive AV conduction detection by increasing the AV conduction check interval at block 212 when a mode switch back to dual chamber pacing occurs within a false AV conduction time interval after the positive AV conduction detection.

In summary, the interval of time at which the next AV conduction check is scheduled will be increased at block 212, relative to an initial shortest conduction check time interval, for at least two conditions: 1) whenever an immediately preceding AV conduction check results in a negative AV conduction detection (block 210) and 2) whenever AV conduction is positively detected but is followed by a mode switch back to dual chamber pacing within a predetermined false AV conduction time interval (block 222). The AV conduction check schedule is reset to an initial shortest interval of time (block 204) only when a mode switch from an atrial pacing mode back to a dual chamber pacing mode occurs after the false AV conduction time interval has expired. In this way, every mode switch to dual chamber pacing does not reset the scheduled AV conduction check schedule to an initial short interval that is increased only when AV conduction is not detected.

The method described in conjunction with flowchart 200 provides for the discrimination of a false positive AV conduction and a true positive AV conduction based on a duration of an atrial-only pacing mode. A short duration of an atrial-only pacing mode, as defined according to a predetermined "false" AV conduction time interval, indicates with high probability that the precipitating AV conduction detection is a false positive detection. An atrial-only pacing mode that is sustained for longer than the predetermined time interval indicates with high probability that the AV conduction detection is a true positive detection. This discrimination of "false" and "true" positive AV conduction detections allows the IMD to respond to the false positive detections and true positive detections differently, providing a more appropriate response to false positive detections, e.g. by increasing the interval until the next AV conduction check.

The increase in the AV conduction check interval at block 212 may be implemented in a number of ways. At a minimum, the method shown in flowchart 200 is intended to avoid resetting the AV conduction check schedule to the initial shortest interval at block 204 when a false positive AV conduction detection is made.

The increase at block 212 may be an increase to the next longer interval in a set of successively increasing conduction check intervals which would normally follow the interval at which the AV conduction check was performed at block 210 and resulted in the false positive AV conduction detection. For example, if the AV conduction check was performed after the initial one minute interval of dual chamber pacing and resulted in a false positive AV conduction detection, the AV conduction check interval may be increased to the next scheduled interval, e.g. two minutes. If the AV conduction check resulting in AV conduction detection was performed at an interval of eight minutes since the last conduction check, and the next conduction check interval in a schedule of successively increasing intervals is sixteen minutes, the interval may be increased to the next successive interval of sixteen minutes. In other words, scheduling AV conduction checks may continue according to a successive schedule of increasing intervals thereby treating a false positive AV conduction detection the same as a negative AV conduction detection as it relates to scheduling AV conduction checks.

The AV conduction check schedule may have reached a maximum interval, e.g., approximately 16 hours, when the false AV conduction detection is made at block 210. In this case, the increased AV conduction check interval applied at block 212 may be to return to the maximum interval until the next scheduled AV conduction check.

In other embodiments, a mode switch back to dual chamber pacing during the false AV conduction time interval may cause the next scheduled AV conduction check to be scheduled at any interval that is greater than the initial shortest interval of a schedule of successively increasing intervals. Continuing with the example given above, if the initial shortest interval for performing an AV conduction check is one minute, the interval at which a next conduction check is scheduled in response to a mode switch back to dual chamber pacing within a false AV conduction time interval may be any interval greater than one minute. The interval may be set regardless of what time interval the AV conduction check resulting in a false AV conduction detection was performed as long as the interval is greater than the initial, shortest interval of a schedule of progressively increasing intervals.

The false AV conduction timer may be a fixed time interval, as generally described above, based at least in part on the criteria set for triggering a mode switch to dual chamber pacing. Alternatively, the false AV conduction timer may be a variable interval that is adjusted based on a history of atrial-only pacing mode durations as indicated by block 217. For example, if the false AV conduction timer is set to an initial default interval, e.g. 15 seconds, and the IMD determines that a pacing mode switch back to a dual chamber mode occurs at slightly longer intervals, e.g. 20 to 25 seconds, for one or more atrial-only pacing mode episodes, the IMD may automatically increase the false AV conduction timer. At block 216, the actions performed for setting the false AV conduction timer may therefore include analyzing the duration of past atrial only pacing modes and setting the false AV conduction timer accordingly. For example, if one or more atrial only pacing modes lasted more than the currently set false AV conduction time interval, e.g. 15 seconds, but less than some maximium false conduction time interval, e.g. one minute, the false AV conduction time interval may be automatically increased. The false AV conduction time interval may be adjusted at block 216 to an interval slightly longer than a past atrial only pacing mode episode duration that was less than the maximum false AV conduction time interval.

Figure 7:
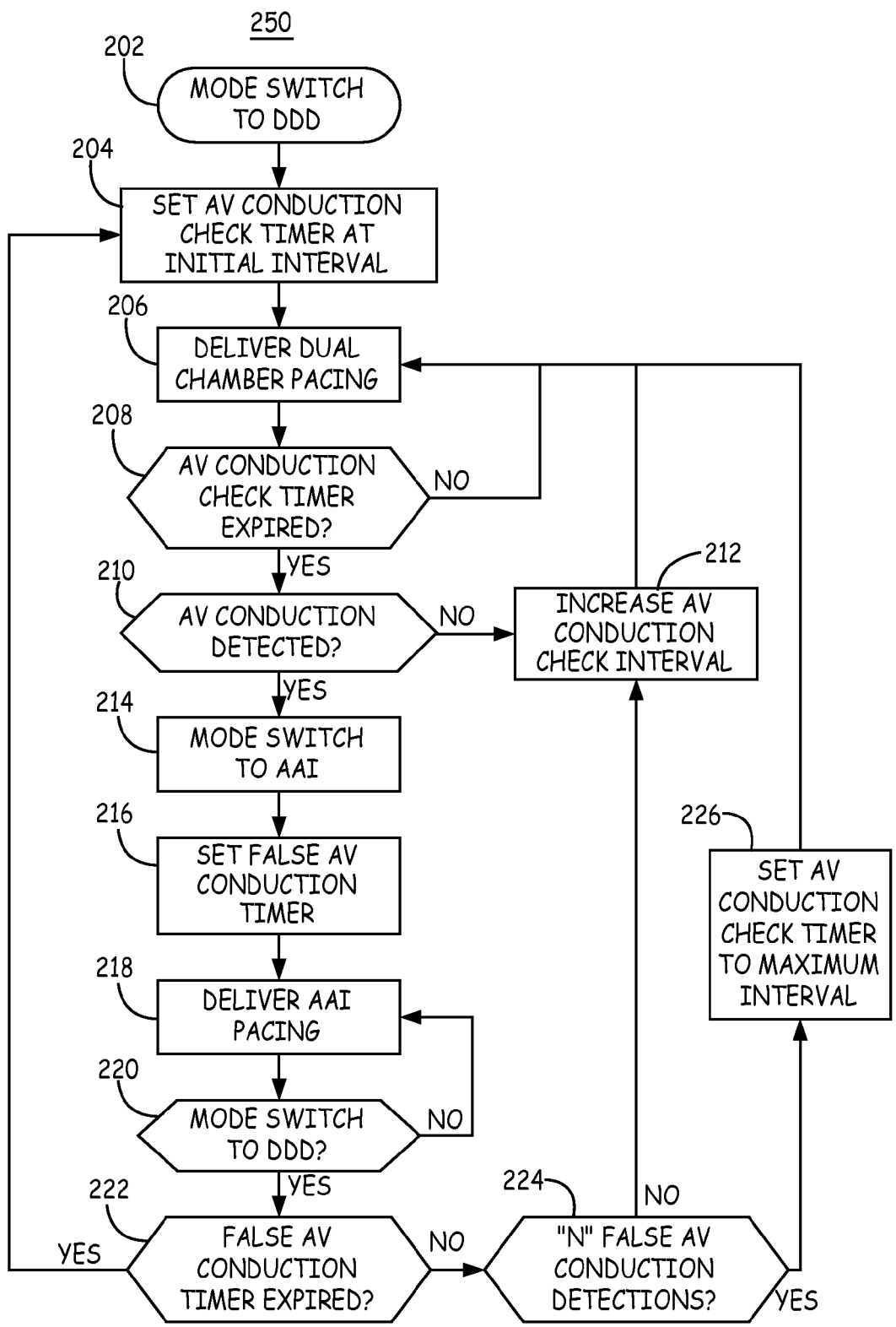
FIG. 7 is a flowchart of an alternative method for controlling minimum ventricular pacing.

FIG. 7 is a flowchart 250 of an alternative method for controlling minimum ventricular pacing. Blocks 202 through 222 in flowchart 250 are the same as in flowchart 200 and are identified by identical reference numerals. In flowchart 250, blocks 224 and 226 are added. In method 250, a counter is used to count the number of false AV conduction detections. At block 224, the number of false positive AV conduction detections made is compared to a predetermined threshold "N". If a predetermined number of false AV conduction detections are made, which may or may not be required to be consecutive false AV conduction detections, the AV conduction check timer may be set to a maximum interval for performing conduction checks at block 226. The maximum interval set in response to a threshold number of false positive AV conduction detections may or may not be the same as a maximum interval of a schedule of successively increasing AV conduction check intervals.

The threshold condition tested at block 224 may be defined as any frequency or number of false positive AV conduction detections. As indicated above, a false positive AV conduction detection is one that is followed by a return to dual chamber pacing within a false AV conduction timer interval. If the number or frequency of mode switches back to a dual chamber pacing mode within the false AV conduction time interval exceeds some predetermined value, the AV conduction check interval may be automatically set to some maximum interval to avoid frequent mode switching and conduction checks.

Figure 8:
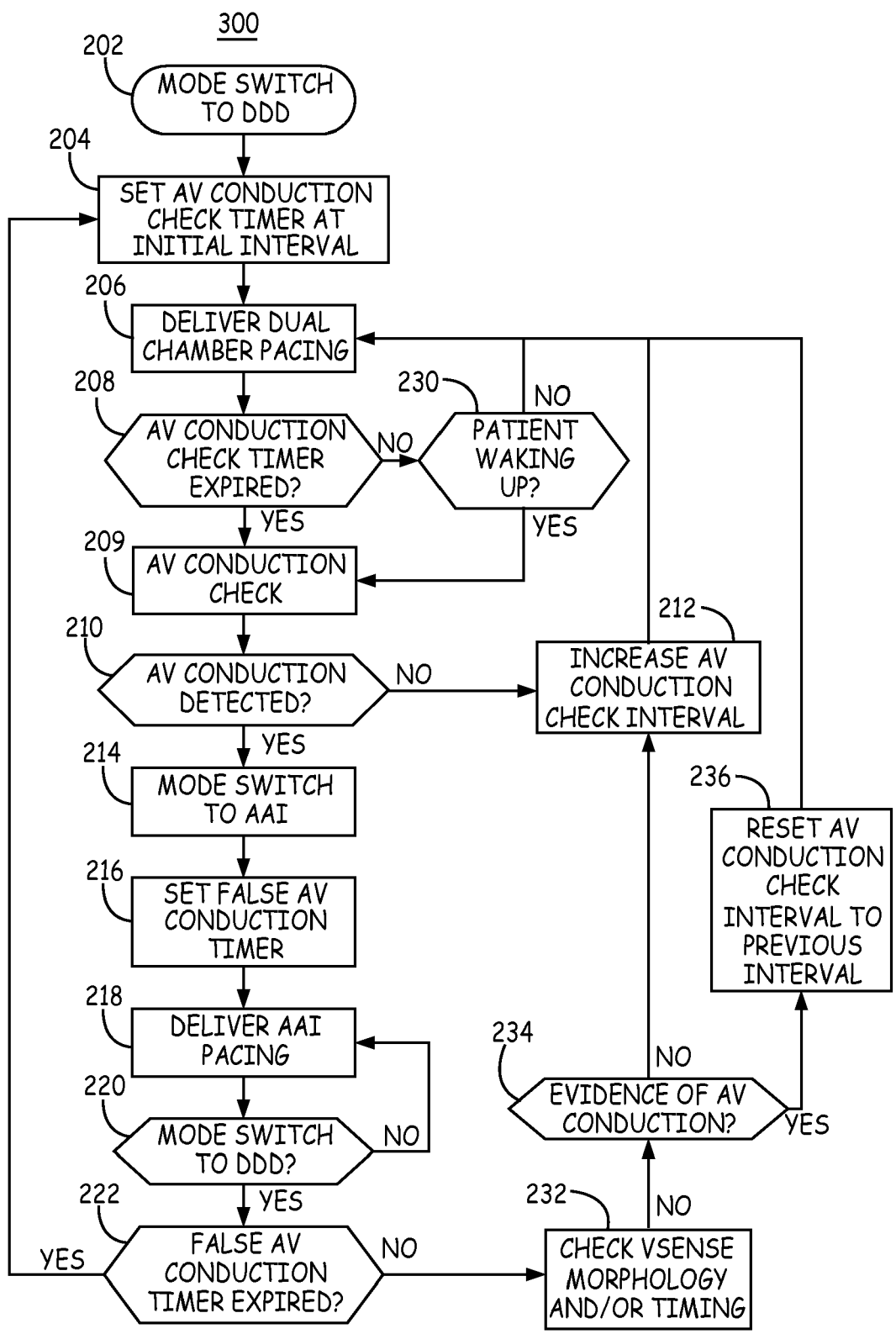
FIG. 8 is a flow chart of yet another method for controlling minimum ventricular pacing.

FIG. 8 is a flow chart 300 of an alternative method for controlling minimum ventricular pacing. Identically numbered blocks 202 through 222 in flow chart 300 correspond to those shown in flow chart 200 and described in conjunction therewith. In flowchart 300, blocks 230, 232, 234 and 236 are added. Some patients may experience highly intermittent AV block, e.g. second degree AV block, particularly at night when the autonomic nervous system down regulates AV conduction. As such, it may be desirable to provide an AV conduction check in the morning when the patient is awake even though the next AV conduction check may not be scheduled for several hours according to a successively increasing AV conduction check interval schedule.

In method 300, block 230 provides a check for determining if the patient is waking up or expected to be awake after a period of likely being asleep. Evidence of a patient waking up or likely to be awake after being asleep may be detected based on the time of day (e.g., a morning hour when the patient is expected to awake or already be awake), a heart rate, an activity sensor, a posture sensor, or any combination thereof. If evidence of a patient waking up or being awake after a period of being asleep is detected, an AV conduction check is performed immediately at block 209 to determine if AV conduction has returned. If no evidence of the patient likely being awake is detected, the dual chamber pacing continues at block 206.

As an illustrative example, if an AV conduction check fails at 23:00 (11:00 at night), conduction checks may be performed at successively increasing intervals at 23:01, 23:03, 23:07, 23:15, 23:31, 00:02, 02:02, 06:02, and 14:00 (2:00 in the afternoon the next day). If AV conduction returns in the morning when the patient awakes, for example at 07:00, the ventricular pacing may be maintained in the dual chamber pacing mode from 07:00 until 14:00 unnecessarily.

A conduction check triggered in response to detecting evidence of the patient waking up could detect a return of AV conduction with the up regulation of the autonomic nervous system and cause a mode switch to atrial-only pacing at block 214. In alternative embodiments, an AV conduction check may be permanently scheduled to occur at a morning hour, such as 8:00 am, inserted in a schedule of progressively increasing AV conduction check intervals, to check for AV conduction each morning. In still other embodiments, detection that the patient is likely to be awake at block 230 may cause the AV conduction check schedule to be reset to an initial shortest interval at block 204.

When AV conduction is positively detected at block 210, method 300 proceeds to blocks 214 through 222 to discriminate between false positive and true positive AV conduction detections as described above. At block 232, additional analysis of the ventricular sensed event that caused the false positive AV conduction detection and/or any ventricular sense events that occur during the subsequent atrial-only pacing mode may be performed to further distinguish between true and false positive AV conduction detections.

The ventricular sensed event(s) may be analyzed at block 232 to discriminate between conducted and non-conducted ventricular sensed events. The morphology and/or the timing of the ventricular sensed event(s) may be examined. A depolarization originating in the ventricular chambers of the heart will have a different morphology than a depolarization that has been conducted from the atria. The AV interval and VV intervals associated with sensed ventricular depolarizations during atrial-only pacing and/or during the AV conduction check may also be examined to determine if the VV intervals between sensed ventricular events represent a regular slow rate, such as a slow idioventricular rate, and if the ventricular depolarizations are associated with the atrial events (paced or sensed) by a regular interval that is within an expected physiological AV conduction time range.

If the morphology and/or timing analysis at block 232 provides evidence of AV conduction at block 234, the next AV conduction check may not be increased even though a mode switch back to dual chamber pacing occurred within the false AV conduction timer. Intermittent AV conduction may be present. In response to evidence of true AV conduction detected at block 234, the AV conduction check interval may be held at the previously scheduled interval at block 236. In other embodiments, the additional analysis providing evidence of AV conduction may cause the AV conduction check to reset at the initial shortest interval at block 204, which may then be increased up to a longer or maximum interval if subsequent false positive AV conduction detections occur, e.g. as described in conjunction with FIG. 7. If no evidence of AV conduction is detected at block 234, the AV conduction check interval is increased at block 212 as described previously.

FIG. 9 is a timeline 400 illustrating the situation of an idioventricular rhythm causing a false positive AV conduction detection. Atrial events are shown in the upper portion of timeline 400 and ventricular events are shown in the lower portion. Initially a dual chamber pacing mode 402 is in effect. In this example, the atrial event 402 is a sensed event to illustrate that the atrial events during dual or single chamber pacing modes may be atrial sensed events when the intrinsic atrial rate exceeds a lower pacing rate. A ventricular pace event 406 follows the atrial sense event 404 at a programmed AV escape interval.

An AV conduction check 401 is performed by withholding ventricular pacing for one cycle following atrial sense event 408. A ventricular sense event 410 occurs during the AV conduction check 401 resulting in a positive AV conduction detection. The positive AV conduction detection causes a mode switch to atrial-only pacing 412. Atrial sense (AS) events 414 continue at a rate faster than a programmed lower rate and thus atrial pacing pulses do not occur during the atrial-only pacing mode in this example.

During the first atrial-only pacing cycle 416, no ventricular event is sensed. During the next atrial-only pacing cycle, a ventricular sense event 418 occurs at an interval 432 that is shorter than the programmed AV escape interval. This ventricular sense event 432 causes inhibition of a ventricular pacing pulse that would normally be delivered at the end of a programmed AV escape interval to prevent more than one cycle of ventricular asystole. Another ventricular sense event 420 occurs during the next atrial-only pacing cycle at an interval 434 following the atrial sense event.

No ventricular sense event occurs during the next atrial-only pacing cycle 422, however, causing a mode switch back to dual chamber pacing 444 in which ventricular pacing pulses 446 are again delivered at a programmed AV escape interval. Because this mode switch occurs within a false AV conduction time interval 448, the AV conduction detection is considered a false positive detection. Additional analysis may be performed at block 232 of flow chart 300 (FIG. 8) to verify the false positive detection. For example, the morphology of the ventricular sense events 410, 418 and 420 may be compared to a morphology template for a known conducted ventricular depolarization. If the morphology matches, the ventricular sense events 410, 418 and 420 may be associated with the atrial sense events as normally conducted events. A morphology mismatch would indicate that the ventricular sense events 410 are not conducted from the atrial chambers.

Alternatively or additionally, time intervals associated with the ventricular sense events 410, 418 and 420 may be examined. In one embodiment, AV intervals 430, 432 and 434 are examined. AV intervals that are similar to each other and fall within an expected physiological AV conduction time range, would be evidence of AV conduction. Typical AV conduction time falls between approximately 100 ms and 350 ms but may be observed as long as approximately 500 ms. An expected AV conduction time range may be tailored to a given patient. In some patients, long AV intervals, e.g. between approximately 350 ms and 500 ms, is likely to be associated with some degree of AV block. Thus such intervals measured during an AV conduction check and/or atrial only pacing may be evidence of intermittent AV conduction in some patients. Very short AV intervals, e.g. less than approximately 100 ms, and very long AV intervals, for example greater than approximately 500 ms, typically occur when the ventricular depolarization is not associated with the atrial event and are likely to be evidence of PVCs or idioventricular events.

AV intervals 430, 432 and 434 which are highly variable (vary from each other by more than a predetermined amount) and/or fall outside an expected physiological AV conduction time range indicate that ventricular sense events 410, 418 and 420 are not likely to be associated with the atrial sense events. This is evidence that the VS events 410, 418 and 420 are non-conducted ventricular depolarizations and may be PVCs or an idioventricular rhythm.

In another embodiment, the VV intervals 440 and 442 between the ventricular sense events 410, 418 and 420 are examined. If the VV intervals 440 and 442 are regular, this may be evidence of an idioventricular rhythm. In particular, the combination of AV dissociation based on the irregular AV intervals 430, 432 and 434 and the regular, relatively long VV intervals 440 and 442 provides evidence of an idioventricular rhythm and supports the finding of a false positive AV conduction detection.

In FIG. 9, the start time 449 of the false AV conduction time interval 448 is shown to occur upon the atrial event 414 that concludes a one-cycle AV conduction check. It is recognized that in various embodiments, the start time 449 may coincide with the first atrial event 408 starting an AV conduction check 401, the time of the mode switch to atrial-only pacing, or other defining start time.

FIG. 10 is a time line 500 illustrating the situation of highly intermittent AV conduction resulting in a positive AV conduction check. Initially a dual chamber pacing mode 502 is in effect. In this example, the atrial event 502 during dual chamber pacing is shown as a paced event due to an intrinsic atrial rate less than a programmed lower pacing rate. It is recognized that the atrial events during atrial-only and dual chamber pacing modes may include both sensed and paced events depending on the underlying intrinsic atrial rate and changes in the intrinsic rate and in a sensor-indicated lower pacing rate. A ventricular pace event 506 follows the atrial sense event 504 at a programmed AV escape interval.

An AV conduction check 501 is performed by withholding ventricular pacing for one cycle following atrial pace event 508. A ventricular sense event 510 occurs during the AV conduction check 501 resulting in a positive AV conduction detection. The positive AV conduction detection causes a mode switch to atrial-only pacing 512. Atrial pace events 514 continue at a programmed lower rate (or sensor indicated lower rate) during the atrial-only pacing 512.

Initially, ventricular sense events 516 and 518 continue to follow the atrial pace events due to intermittent intact AV conduction. However, during a next atrial-only pacing cycle 520, no ventricular sense event occurs. A ventricular pacing pulse 524 is delivered during the next atrial-only pacing cycle to prevent another cycle of ventricular asystole. Another atrial-only pacing cycle 522 without a ventricular sense event causes a mode switch back to dual chamber pacing 544 in which ventricular pacing pulses 546 are again delivered at a programmed AV escape interval. Because this mode switch back to dual chamber pacing 544 occurs within a false AV conduction time interval 548, the AV conduction detection is considered a false positive detection.

Additional analysis may be performed at block 232 of flow chart 300 (FIG. 8) to verify the false positive detection. For example, the morphology of the ventricular sense events 510, 516 and 518 may be compared to a morphology template for a known conducted ventricular depolarization. A morphology match would be evidence of AV conduction indicating that the AV conduction detection may be a true conduction caused by intermittent AV conduction (second degree AV block).

Alternatively or additionally, time intervals associated with the ventricular sense events 510, 516 and 518 may be examined. In one embodiment, AV intervals 530, 532 and 534 are examined. In this example, AV intervals 530, 532 and 534 are similar to each other and fall within an expected physiological AV conduction time range. This is evidence of intact AV conduction since the ventricular sense events 510, 516, and 518 are each associated with an atrial pace event by a predictable conduction time. Likewise, the VV intervals 540 and 542 between the ventricular sense events 510, 516, and 518 are regular and associated with the AA intervals in a 1:1 correspondence. Any of these findings of a ventricular depolarization morphology similar to a known conducted ventricular depolarization morphology, predictable AV intervals associating the ventricular sense events with atrial events, and/or regular VV intervals having 1:1 correspondence with atrial events is evidence of true AV conduction.

This evidence may be used to reclassify the initial AV conduction check result as a true positive AV conduction but note that the conduction is likely associated with intermittent AV block. The response of the IMD may be to set the next AV conduction interval at a longer interval than the initial shortest interval of a schedule of progressively increasing intervals as generally described in conjunction with FIG. 8. Data corresponding to true and false AV conduction checks may be stored in IMD memory such that it is available to a clinician for evaluating the AV conduction status of the patient.

In FIG. 10, the false AV conduction timer is shown embodied as a counter instead of a timer based units of time. In this embodiment, the false AV conduction time interval 548 counts each cardiac cycle during the atrial-only pacing mode 512. With each atrial pace event, the counter is increased by one. If the pacing mode switch back to dual chamber pacing 544 occurs within a predetermined number of cycles, eight cycles in the illustrative example shown, the positive AV conduction detection is classified as a false detection. If the counter exceeds the predetermined number of cycles, the AV conduction detection is classified as true. As used herein, a false AV conduction time interval, therefore, may be an interval defined in units of time or an interval defined as a number of cardiac cycles occurring during an atrial-only pacing mode.

Thus, a medical device and associated methods relating to AV conduction checks have been presented in the foregoing description with reference to specific embodiments. In general, the methods described herein allow for discrimination of true and false positive AV conduction detections and thereby provide a more appropriate response to false positive AV conduction detections. The response to false positive AV conduction detection can include minimizing frequent mode switching and AV conduction checks during minimum ventricular pacing in the presence of frequent PVCs, an idioventricular rhythm, or non-conducted events sensed as ventricular depolarizations that result in positive AV conduction detections. It is appreciated that various modifications to the referenced embodiments may be made without departing from the scope of the disclosure as set forth in the following claims.

The invention claimed is:

1. A method for delivering a cardiac pacing therapy by an implantable device, comprising:
   delivering cardiac pacing in a dual chamber pacing mode;
   performing an atrial-ventricular (AV) conduction check during the dual chamber pacing mode to detect AV conduction;
   switching to an atrial pacing mode in response to detecting the AV conduction;
   setting an interval of time for use in identifying false positive AV conduction detections in response to detecting the AV conduction;
   sensing a ventricular signal to detect ventricular sense events;
   switching back to the dual chamber pacing mode in response to not detecting a ventricular sensed event during an atrial pacing cycle; and
   identifying the detected AV conduction as a false positive detection in response to the pacing mode switching back to the dual chamber pacing mode within the set interval of time.

2. The method of claim 1 further comprising:
   scheduling the AV conduction check to be repeated at successively increasing intervals of time when AV conduction is not detected during an AV conduction check; and
   increasing a scheduled interval of time until a next AV conduction check in response to identifying the false positive detection.

3. The method of claim 2 wherein increasing a scheduled interval of time until a next AV conduction check comprises increasing the interval of time to a next interval of the successively increasing intervals.

4. The method of claim 2 wherein increasing a scheduled interval of time until a next AV conduction check comprises increasing the interval of time to a maximum of the successively increasing intervals.

5. The method of claim 2 wherein increasing a scheduled interval of time until a next AV conduction check comprises increasing the interval of time to an interval greater than an initial shortest interval of the successively increasing intervals.

6. The method of claim 2 further comprising:
   analyzing one of a ventricular sense event morphology and a ventricular sense time interval in response to identifying the detected AV conduction as a false positive detection;
   identifying evidence of AV conduction in response to the analyzing; and
   identifying the AV conduction detection as a true positive AV conduction detection in response to identifying the evidence of AV conduction.

7. The method of claim 1 further comprising:
   determining if a patient is likely to be awake after a period of being asleep; and
   performing an AV conduction check in response to determining the patient is likely to be awake.

8. The method of claim 1 wherein setting the time interval comprises determining a duration of a previous atrial pacing mode episode.

9. An implantable device for delivering a cardiac pacing therapy, comprising;
   an atrial pacing and sensing lead for delivering atrial pacing pulses and sensing atrial signals;
   a ventricular pacing and sensing lead for delivering ventricular pacing pulses and sensing ventricular signals;
   a sensing module coupled to the atrial and ventricular pacing and sensing leads, the sensing module responsive to depolarizations of a heart;
   a pulse generator producing cardiac stimulation pulses delivered via the atrial and ventricular pacing and sensing leads; and
   a control module coupled to the sensing module and the therapy delivery module, the control module capable of switching between a dual chamber pacing mode and an atrial pacing mode and configured to:
      deliver cardiac pacing in the dual chamber pacing mode;
      perform an atrial-ventricular (AV) conduction check during the dual chamber pacing mode to detect AV conduction;
      switch to the atrial pacing mode in response to detecting the AV conduction;
      set an interval of time for use in identifying false positive AV conduction detections in response to detecting the AV conduction;
      sense a ventricular signal to detect ventricular sense events;
      switch back to the dual chamber pacing mode in response to not detecting a ventricular sensed event during an atrial pacing cycle; and
      identify the detected AV conduction as a false positive detection in response to the pacing mode switching back to the dual chamber pacing mode within the set interval of time.

10. The device of claim 9 wherein the control module is configured to schedule the AV conduction check to be repeated at successively increasing intervals of time when AV conduction is not detected during an AV conduction check; and to increase a scheduled interval of time until a next AV conduction check in response to identifying the false positive detection.

11. The device of claim 10 wherein increasing a scheduled interval of time until a next AV conduction check comprises increasing the interval of time to a next interval of the successively increasing intervals.

12. The device of claim 10 wherein increasing a scheduled interval of time until a next AV conduction check comprises increasing the interval of time to a maximum of the successively increasing intervals.

13. The device of claim 10 wherein increasing a scheduled interval of time until a next AV conduction check comprises increasing the interval of time to an interval greater than an initial shortest interval of the successively increasing intervals.

14. The device of claim 10 wherein the control module is further configured to analyze one of a ventricular sense event morphology and a ventricular sense event time interval in response to identifying the detected AV conduction as a false positive detection; to identify evidence of AV conduction in response to the analyzing; and to identify the AV conduction detection as a true positive AV conduction detection in response to identifying the evidence of AV conduction.

15. The device of claim 9 further comprising:
means for determining if a patient is likely to be awake after a period of being asleep;
the control module further configured to perform an AV conduction check in response to determining the patient is likely to be awake.

16. The device of claim 9 wherein the control module is configured to determine a duration of a previous atrial pacing mode episode and set the time interval using the duration of the previous atrial pacing mode episode.

17. A non-transitory computer readable medium storing a set of instructions which when implemented in a cardiac medical device cause the device to:
deliver cardiac pacing in a dual chamber pacing mode;
perform an atrial-ventricular (AV) conduction check during the dual chamber pacing mode to detect AV conduction;
switch to an atrial pacing mode in response to detecting the AV conduction;
set an interval of time for use in identifying false positive AV conduction detections in response to detecting the AV conduction;
sense a ventricular signal to detect ventricular sense events;
switch back to the dual chamber pacing mode in response to not detecting a ventricular sensed event during an atrial pacing cycle; and
identify the detected AV conduction as a false positive detection in response to the pacing mode switching back to the dual chamber pacing mode within the set interval of time.

18. The non-transitory computer readable medium of claim 17 further storing instructions which cause the device to:
schedule the AV conduction check to be repeated at successively increasing intervals of time when AV conduction is not detected during an AV conduction check; and
increase a scheduled interval of time until a next AV conduction check in response to identifying the false positive detection.

* * * * *